United States Patent
Stawitz et al.

(10) Patent No.: US 6,420,576 B1
(45) Date of Patent: Jul. 16, 2002

(54) PREPARATION OF ARYLAMINOHYDROXYANTHRAQUINONES

(75) Inventors: Josef-Walter Stawitz; Stephan Michaelis, both of Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/625,567

(22) Filed: Jul. 26, 2000

(30) Foreign Application Priority Data

Aug. 2, 1999 (DE) .......................................... 199 36 282

(51) Int. Cl.$^7$ ................................................ C09B 1/06
(52) U.S. Cl. ........................ 552/247; 552/238; 552/243
(58) Field of Search ................................. 552/238, 243, 552/247

(56) References Cited

U.S. PATENT DOCUMENTS 3,436,410 A * 4/1969 Weinand et al. ............ 260/373

FOREIGN PATENT DOCUMENTS

| GB | 1174885 | | 12/1969 |
| GB | 1184375 | * | 3/1970 |
| GB | 1527383 | | 6/1977 |

* cited by examiner

Primary Examiner—Alton N Pryor
(74) Attorney, Agent, or Firm—Joseph C. Gil; Thomas W. Roy

(57) ABSTRACT

The process for preparing arylaminohydroxyanthraquinone of the formula

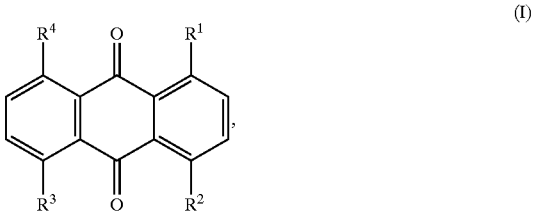

(I)

by reacting appropriate chlorohydroxyanthraquinone with an amine of the formula (III)

$$H_2N—Ar \quad (III),$$

is characterized in that one mole of amine of the formula (III) plus an excess of 10 to 100% based on one mole of amine is used per chlorine atom in the compounds of the formula (II) and the reaction is carried out in an inert solvent in the presence of a base selected from the group consisting of the carbonates of the alkali and alkaline earth metals, the acetates of the alkali metals, the phosphates of the alkali metals and any mixtures thereof.

6 Claims, No Drawings

PREPARATION OF ARYLAMINOHYDROXYANTHRAQUINONES

The present invention relates to a novel process for preparing arylaminohydroxyanthraquinones.

BACKGROUND OF THE INVENTION

The condensation of arylamines with chlorohydroxyanthraquinones is well known; see NL-A-6 504 570 and GB-A-1 527 383. However, these processes have serious disadvantages.

NL-A-6 504 570 utilizes the arylamine in high excess and hence also as solvent. This leads to high amine contents of above 1% in the dye, so that for many applications (coloration of children's toys, food packaging, etc) it is absolutely necessary to redissolve the dye in another solvent. Furthermore, the dye quality obtained does not meet present-day requirements with regard to brilliance. In GB-A-1 527 383, arylaminohydroxyanthraquinones are prepared from chlorohydroxyanthraquinones and arylamines in an inert solvent (eg ethoxyethanol) using boric acid and an excess of arylamine as base. The dye obtained from this process likewise is not of adequate quality and would have to be subjected to further purification steps, for example a recrystallization.

There has now been found a process whereby arylaminohydroxyanthraquinones can be prepared in very good yields and in high purity without the abovementioned disadvantages.

SUMMARY OF THE INVENTION

The present invention accordingly provides a process for preparing arylaminohydroxyanthraquinones of the formula (I)

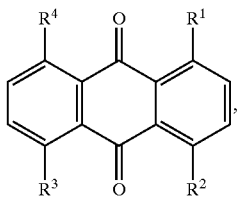

(I)

where
$R^1$, $R^2$, $R^3$ and $R^4$ are independently hydrogen, hydroxyl or NH—Ar, where
Ar is an aryl radical optionally substituted by one or more, identical or different substituents,
with the proviso that at least one of $R^1$ to $R^4$ is OH and at least one of $R^1$ to $R^4$ is —NH—Ar,
by reacting appropriate chlorohydroxyanthraquinones of the formula (II)

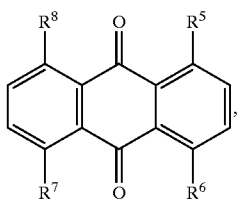

(II)

where
$R^5$, $R^6$, $R^7$ and R8 are independently hydrogen, chlorine or hydroxyl,
with the proviso that at least one of $R^5$ to $R^8$ is chlorine and at least one of $R^5$ to $R^8$ is hydroxyl,
with an amine of the formula (III)

$$H_2N—Ar \qquad (III),$$

where
Ar is as defined above,
characterized in that one mole of amine of the formula (III) plus an excess of 10 to 100% based on one mole of amine is used per chlorine atom in the compounds of the formula (II) and the reaction is carried out in an inert solvent in the presence of a base selected from the group consisting of the carbonates of the alkali and alkaline earth metals, the acetates of the alkali metals, the phosphates of the alkali metals and any mixtures thereof.

DETAILED DESCRIPTION OF THE INVENTION

The compounds of the formula (II) are preferably 1-chloro-4-hydroxyanthraquinone, 4,8-dichloro-1,5-dhydroxyanthraquinone, 4,5-dichloro-1,8-dihydroxyanthraquinone, 8-chloro-1,4,5-trihydroxyanthraquinone or 5,8-dichloro-1,4-dihydroxyanthraquinone.

The aforementioned chlorohydroxyanthraquinones of the formula (II) are generally used in pure form for the process of the invention. However, it is also possible, with similar success, to use the compounds (II) in the form of technical-grade material.

This technical-grade material, as well as compounds of the formula (II), will then generally additionally contain 15 to 25% of impurities in the form of more highly substituted products and/or products which are isomeric to the formula (II).

The process of the invention is preferably carried out using 5,8-dichloro-1,4-dihydroxyanthraquinone in the form of technical-grade material. The chlorine atoms in the by-products present in the technical-grade material will likewise be replaced by amino groups in the course of the reaction with the amine (III) according to the invention. These reaction products, however, remain in the mother liquor and can be removed with the mother liquor from the products (I) prepared according to the invention and thus do not constitute an impairment to the quality of the end product.

More particularly, Ar is naphthyl optionally substituted by one or more identical or different substituents selected from the group consisting of alkyl and halogen or is phenyl optionally substituted by one or more identical or different substituents selected from the group consisting of cyano, carboxyl, nitro, alkylsulphonyl, carbonyl, sulfo, alkylaminocarbonyl, alkylcarbonylamino, alkyl, cycloalkyl, alkoxy, trifluoromethyl, halogen and aryl, which in turn may be substituted by the radicals mentioned above for naphthyl and phenyl.

Alkyl, alone or as part of compound terms such as alkylsulphonyl, alkylaminocarbonyl and alkylcarbonylamine, is especially straight-chain or branched $C_1$ to $C_6$-alkyl. Cycloalkyl is especially cyclopentyl or cyclohexyl. Alkoxy is preferably straight-chain or branched $C_1$- to $C_6$-alkoxy. Aryl is especially phenyl or naphthyl. Halogen is preferably chlorine or bromine.

Preferred substituents for phenyl and naphthyl are methyl, ethyl, n-propyl, isopropyl, n-butyl, sec-butyl, tert-butyl, cyclohexyl, methoxy, chlorine, bromine and phenyl, which may in turn be substituted. Particular preference is given to methyl, tert-butyl, n-butyl, cyclohexyl and phenyl.

The arylamines (III) are used in the theoretically required amount plus an excess of preferably 10 to 50%, particularly preferably 10 to 30%, especially preferably 10 to 20%, based on 1 mol of arylamine.

Preferred inert solvents are:

N-methylpyrrolidone, chlorobenzene, 1,2-dichlorobenzene, 1,2,4-trichlorobenzene, xylene, nitrobenzene and phenol.

Particular preference is given to N-methylpyrrolidone and dichlorobenzene.

Preferred bases are sodium carbonate, potassium carbonate, sodium acetate, potassium acetate, trisodium phosphate, disodium hydrogenphosphate and sodium dihydrogenphosphate or mixtures of the carbonates with acetates and mixtures of the carbonates with the phosphates.

Particular preference is given to disodium hydrogenphosphate, trisodium phosphate and mixtures of sodium carbonate with sodium acetate. The amount of base used is generally from 0.5 to 2.5 equivalents of base, preferably 0.5 to 1 equivalent, per chlorine atom to be replaced in the compounds of the formula (II) or per mole of hydrochloric acid released.

The reaction is carried out at a temperature between 80° and 200° C., preferably between 110° and 190° C.

The impurities remain dissolved in the mother liquor and are virtually completely removed in the course of isolation by filtration and washing of the residue by displacement of the mother liquor.

The process of the invention provides the arylaminohydroxyanthraquinones in very good yield of 80 to 100%, preferably >90%, with the level of impurities due to amine (III) being less than 600 ppm, preferably less than 300 ppm.

The compounds of the formula (I) are useful dyes for the transparent and hiding coloration of plastics such as polystyrene, polyamide, polycarbonate, polyethylene, polyester, eg polyethylene terephthalate or polyethylene butylate, ABS and ABS-PC blends. They are used not only for mass coloration but also for spin dyeing.

EXAMPLES

Example 1

A mixture of 93.0 parts of 5,8-dichloro-1,4-dihydroxyanthraquinone (technical-grade material, 80% pure), 300 parts of 1,2-dichlorobenzene, 108 parts of p-tert-butylaniline and 22.5 parts of disodium hydrogenphosphate is heated under nitrogen to 150° C. in the course of an hour and maintained at 150° C. for one hour.

The mixture is then heated to 170° C. in the course of one hour and maintained at 170° C. for two hours. The temperature is then raised to 180° C. and maintained there for 12 hours. After cooling to 90° C., 375 parts of methanol are added dropwise in the course of 1 h in such a way that the batch is maintained at 65 to 68° C. The batch is subsequently stirred under reflux for one hour, cooled down to 25° C., stirred at 25° C. for two hours and suction-filtered.

The dye is washed with 270 parts of a 2:1 mixture of methanol and dichlorobenzene, then with 375 parts of hot methanol (65° C.) and then with 1000 parts of water (80° C.). The moist product is dried at 70° C. under reduced pressure, affording 126.8 parts of the dye of the following formula

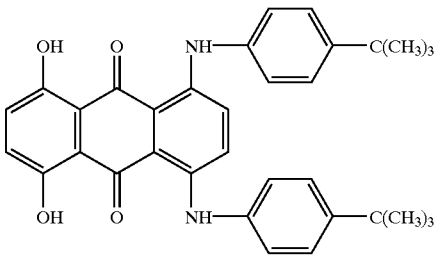

that is 98.6% of theory, based on the main component of the 5,8-dichloro-1,4-dihydroxyanthraquinone used.

The dye contains <100 ppm of p-tert-butylaniline.

Example 2

A mixture of 93.0 parts of 5,8-dichloro-1,4-dihydroxyanthraquinone (technical-grade material, 80% pure), 250 parts of N-methylpyrrolidone, 112 parts of p-tert-butylaniline and 85.2 parts of disodium hydrogenphosphate is heated under nitrogen to 150° C. in the course of an hour and maintained at 150° C. for three hours.

The mixture is then heated to 180° C. in the course of one hour and maintained at 180° C. for 12 hours. After cooling to 120° C., 375 parts of methanol are added dropwise in the course of 1 h in such a way that the batch is maintained at 65 to 68° C. The batch is subsequently stirred under reflux for one hour, cooled down to 55° C., stirred at 55° C. for two hours and suction-filtered.

The suction-filter cake is washed with 115 parts of a 2:3 mixture of methanol and N-methylpyrrolidone to displace the mother liquor. It is then washed with 1000 parts of hot methanol (65° C.) and 1000 parts of water (80° C). The moist product is dried at 70° C. under reduced pressure, affording 120.6 parts of the pure dye, that is 93.8% of theory.

The dye contains <50 ppm of p-tert-butylaniline.

What is claimed is:

1. A process for preparing an arylaminohydroxyanthraquione of formula (I)

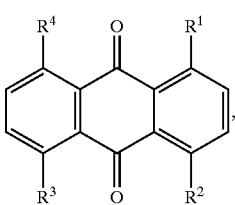

wherein
R$^1$, R$^2$, R$^3$ and R$^4$ are independently hydrogen, hydroxyl or NH—Ar, provided that at least one of R$^1$ to R$^4$ is OH and at least one of R$^1$ to R$^4$ is —NH— Ar, and Ar is naphthyl; naphthyl substituted by one or more identical or different substituents selected from the group consisting of alkyl and halogen; phenyl; and/or phenyl substituted by one or more identical or different substituents selected from the group consisting of cyano, carboxyl, nitro, alkylsulphonyl, carbonyl, sulfo, alkylaminocarbonyl, alkylcarbonylamino, alkyl, cycloalkyl, alkoxy, trifluoromethyl, halogen and aryl, which in turn may be substituted by the radicals mentioned above for naphthyl and phenyl, which comprises reacting a chlorohydroxyanthraquinone selected from the group consisting of 4,8-dichloro-1,5-dihydroxyanthrachinone, 4,5,-dichloro-1,8-dihydroxyanthrachinone, 5,8-dichloro-1,4-dihydroxyanthrachinone,
with an amine of formula (III),

$$H_2N—Ar \qquad (III),$$

in an amount of 1.1 to 2 moles of amine of formula (III) for each chlorine atom in the chlorohydroxyanthraquinone, wherein the reaction is carried out in an inert solvent comprising a member selected from the group consisting of N-methylpyrrolidone, chlorobenzene, dichlorobenzene, 1,2,4-trichlorobenzene, xylene, nitrobenzene and phenol in the presence of a base comprising a member selected from the group consisting of alkali and alkaline earth metal carbonates, alkali metal acetates and alkali metal phosphates.

2. The process of claim 1 wherein the chlorohydroxyanthraquinone comprises 5,8-dichloro-1,4-dihydroxyanthraquinone.

3. The process of claim 1 wherein amine (III) comprises p-tert-butylaniline.

4. The process of claim 1 wherein the base comprises disodium hydrogenphosphate, trisodium phosphate or a mixture of sodium carbonate and sodium acetate.

5. The process of claim 1 wherein the reaction is carried out at a temperature between 80° and 200° C.

6. The process of claim 2 which comprises reacting 1 mole of 5,8-dichloro-1,4-dihydroxyanthraquinone with 2.4 moles of p-tert-butylaniline in 1,2-dichlorobenzene or N-methylpyrrolidone in the presence of disodium hydrogenphosphate.

* * * * *